(12) United States Patent
Peng

(10) Patent No.: US 11,471,374 B2
(45) Date of Patent: Oct. 18, 2022

(54) MEDICINE APPLICATION DEVICE WITH ULTRASONIC MASSAGE ENABLING CONCENTRATED SUPPLY OF MEDICINE

(71) Applicant: Zhijun Peng, Guangdong (CN)

(72) Inventor: Zhijun Peng, Guangdong (CN)

(*) Notice: Subject to any disclaimer, the term of this patent is extended or adjusted under 35 U.S.C. 154(b) by 75 days.

(21) Appl. No.: 16/824,652

(22) Filed: Mar. 19, 2020

(65) Prior Publication Data

US 2020/0360227 A1    Nov. 19, 2020

(30) Foreign Application Priority Data

May 17, 2019 (CN) .......................... 201910413695.9

(51) Int. Cl.
*A61H 23/02* (2006.01)
*A61M 11/00* (2006.01)
*A61M 11/04* (2006.01)

(52) U.S. Cl.
CPC ....... *A61H 23/0245* (2013.01); *A61M 11/005* (2013.01); *A61M 11/041* (2013.01); *A61H 2201/165* (2013.01); *A61H 2201/1619* (2013.01); *A61H 2201/1623* (2013.01)

(58) Field of Classification Search
CPC ................ A61H 23/0245; A61H 23/02; A61H 2201/1619; A61H 2201/1623; A61H 2201/165; A61H 2201/105; A61H 2201/1215; A61H 2201/0142; A61H 2201/1659; A61H 2205/083; A61H 2205/084; A61H 1/00; A61H 33/06; A61H 39/06; A61H 2033/061; A61H 2033/068; A61H 2201/0207; A61M 2037/0007; A61M 11/005; A61M 11/041; A61M 11/006; A61M 11/04; A61M 11/042; A61M 37/0092; A61M 37/00; A61M 35/003; B65D 83/72

USPC ........................................................ 222/146.2

See application file for complete search history.

(56) References Cited

U.S. PATENT DOCUMENTS

| | | | | |
|---|---|---|---|---|
| 2,869,158 A | * | 1/1959 | Sivells | A61H 7/004 401/28 |
| 2,975,464 A | * | 3/1961 | Abrahamy | B43M 11/06 401/199 |
| 5,730,705 A | * | 3/1998 | Talish | A61F 2/28 601/2 |
| 6,478,754 B1 | * | 11/2002 | Babaev | A61M 35/30 601/2 |
| 8,932,198 B1 | * | 1/2015 | You | A61H 33/6036 600/27 |
| D733,321 S | * | 6/2015 | Somers | A61F 2/28 D24/234 |
| 11,123,577 B2 | * | 9/2021 | Blanche | A61N 7/00 |

(Continued)

*Primary Examiner* — Justine R Yu
*Assistant Examiner* — Kelsey E Baller

(57) ABSTRACT

A medicine application device with ultrasonic massage enabling concentrated supply of medicine, including a medicine concentrated supply device, at least one ultrasonic massage mechanism, a medicine supply pipe and power cables. The ultrasonic massage mechanism has a shell, a base panel having massage projections, and an electrical ultrasonic vibration element; the medicine concentrated supply device has a housing, a control panel, a circuit board, and a medicine supply device. The medicine application device provides high frequency ultrasonic massage and applies medicinal therapy to patients.

5 Claims, 11 Drawing Sheets

(56) References Cited

U.S. PATENT DOCUMENTS

| | | | |
|---|---|---|---|
| 2002/0159916 A1* | 10/2002 | Whitby | A61L 9/035 |
| | | | 422/4 |
| 2019/0083671 A1* | 3/2019 | McDonnell | A61M 21/02 |
| 2019/0148036 A1* | 5/2019 | Royston | H02G 3/0412 |
| | | | 174/17 R |

* cited by examiner

MEDICINE APPLICATION DEVICE WITH ULTRASONIC MASSAGE ENABLING CONCENTRATED SUPPLY OF MEDICINE

BACKGROUND OF THE INVENTION

The present invention relates to the field of electrical products used as medicinal therapy aid, and more specifically relates to an electrical medicine application device.

In the field of traditional Chinese medicinal therapy, moxibustion is the most traditional means and a commonly used method in Chinese medicinal therapy and general health maintenance. Moxibustion makes use of the heat of burning *Artemisia argyi* (Mugwort) felt through a patient's skin to achieve various health benefits such as warming and clearing of the patient's meridian system, activating qi (vital energy) and stimulating blood flow of the body, mitigating dampness and coldness, soothing menstrual pain, balancing yin and yang, promoting blood circulation, and regulating internal organs. In general, moxibustion can effectively facilitate human body metabolism and strengthen our immune system. Nowadays, an electrical therapeutic product that adopts electrical heating for the purpose of moxibustion can be occasionally found in the market, and such product is operated by means of PTC heating, wherein mugwort is first processed into a solid mugwort cake, during use, the mugwort cake is placed on the PTC heater trough of the product to heat up the mugwort cake such that molecules of the mugwort can be volatilized and released to warm the patient's skin. The electrical principle of this kind of prior art product has substantially no difference from that of electrical mosquito repellent and repellent plate. Compared with even more traditional means of carrying out moxibustion, this kind of prior art product can effectively prevent harmful effect to the lung and to the indoor environment due to the smoke produced by burning mugwort, thereby simplifying the procedure of moxibustion and reducing injuries caused by the burning mugwort, however, the therapeutic effects achieved by this kind of prior art product are not greatly enhanced compared to traditional moxibustion. After all, this kind of prior art product is still making use of rising temperature which allows expansion of skin pores following the gradual increase of warming temperature, so that the skin is passively warmed by the heat of mugwort to achieve the therapeutic effects of moxibustion. This kind of passive warming of the skin by the heat of mugwort is deficient largely because of its low effectiveness and poor results. Hence, patients are required to passively receive a longer period of moxibustion treatment before getting some results. Therefore, patients are required to spend more time and money before they can experience some therapeutic effects. Moreover, a specifically designed wearable structure is not provided for the prior art product, instead, the prior art product is now fixed to a targeted human body part to perform moxibustion by simply using tightening straps, which is very inconvenient to use. For example, the prior art product is very difficult to be fixedly attached to body parts like shoulders, cervical vertebrae or head to perform moxibustion, thereby being very inconvenient to use and significantly affecting the therapeutic results.

BRIEF SUMMARY OF THE INVENTION

In view of the aforesaid disadvantages now present in the prior art, the present invention provides a medicine application device with ultrasonic massage enabling concentrated supply of medicine. The device can on one hand apply high frequency ultrasonic massage to the patient's body, and on the other hand apply medicinal therapy. Due to high frequency ultrasonic massage, blood flow of the body can be speeded up, causing quick increase in temperature of the body part being massaged, thus the skin pores thereon will be quickly expanded to actively receive warming from the medicinal molecules. Therefore, therapeutic components of the medicine can quickly and effectively get into the patient's skin to demonstrate the therapeutic effects of the medicine. Thus, the therapeutic results of the medicine can be significantly improved.

The present invention is achieved as follows: A medicine application device with ultrasonic massage enabling concentrated supply of medicine, comprising a medicine concentrated supply device, at least one ultrasonic massage mechanism, a medicine supply pipe and power cables; wherein the ultrasonic massage mechanism comprises a shell, a base panel having massage projections, and an electrical ultrasonic vibration element; the base panel is mounted at a bottom part of the shell; the electrical ultrasonic vibration element is mounted on the base panel; the massage projections make high frequency ultrasonic vibration to perform massage when driven by the electrical ultrasonic vibration element; the electrical ultrasonic vibration element is a high frequency vibrating motor or an ultrasonic transducer. The medicine concentrated supply device comprises a housing, a control panel, a circuit board, and a medicine supply device; wherein the control panel is provided on a surface of the housing; the circuit board is mounted inside the housing; the control panel and the circuit board are electrically connected. The medicine supply device is mounted in the housing and is electrically connected with the circuit board; the medicine supply device is connected with the ultrasonic massage mechanism via the medicine supply pipe to supply medicine to the ultrasonic massage mechanism; a plurality of medicine release holes are provided on the base panel to release medicine; the electrical ultrasonic vibration element is electrically connected with the circuit board via the power cables. The medicine concentrated supply device is implemented as an electrically heating and volatilizing device for solid form medicine, comprising a medicine chamber, an electrical heating plate, and a booster fan, so that medicine molecules are volatilized from the solid form medicine by using the electrical heating plate and then supplied to the ultrasonic massage mechanism. Alternatively, the medicine supply device is implemented as a liquid form medicine spraying device, comprising a liquid storage box, a liquid suction pump and a plurality of mist spray nozzles; the mist spray nozzles are mounted at the ultrasonic massage mechanism; by using the liquid suction pump and the mist spray nozzles, the liquid form medicine is pressurized and ejected as mist to supply to the ultrasonic massage mechanism. Alternatively, the medicine supply device is implemented as an ultrasonically atomized liquid form medicine spraying device, comprising a liquid storage box, an ultrasonic atomizing module, and a booster fan, so that the ultrasonic atomizing module atomizes the liquid form medicine ultrasonically, and the atomized liquid form medicine is supplied to the ultrasonic massage mechanism. Alternatively, the medicine supply device is implemented as an electrical heating and volatilizing device for liquid form medicine, comprising a liquid storage container, an electrical heating ring, a liquid suction body, and a booster fan, wherein one end of the liquid suction body is configured to be inserted into the liquid storage container, and another end of the liquid suction body 249 is configured to be sleeved within the electrical heating ring, so that the electrical heating ring volatilizes the liquid medicine to give out medicine molecules and then supplies the medicine molecules to the ultrasonic massage mechanism.

The present invention has the following beneficial effects: The present invention provides a medicine concentrated supply device of a specific structure to operate cooperatively with a plurality of ultrasonic massage mechanisms, so that the medicine concentrated supply device and the ultrasonic massage mechanisms are organically integrated to offer a brand new therapeutic and health maintenance solution that enables synchronized ultrasonic massage and medicinal therapy. During operation, the present invention can on one hand apply high frequency ultrasonic massage to the patient's body, and on the other hand apply medicinal therapy. Due to high frequency ultrasonic massage, blood flow of the body can be speeded up, causing quick increase in temperature of the body part being massaged, thus the skin pores thereon will be quickly expanded to actively receive warming from the medicinal molecules. Therefore, therapeutic components of the medicine can quickly and effectively get into the patient's skin to demonstrate the therapeutic effects of the medicine. Thus, the therapeutic results of the medicine can be significantly improved. Further, the treatment period can be significantly shortened, thus saving time and money for the patients. The ultrasonic massage mechanism can also produce the effect of blood cavitation, thus obtaining the therapeutic effects of clearing the patient's meridian system, regulating qi (vital energy) and blood of the body, soothing and pain relieving, fighting off fatigue and rectifying body functional mechanisms.

DETAILED DESCRIPTION OF THE INVENTION

Figure 1:
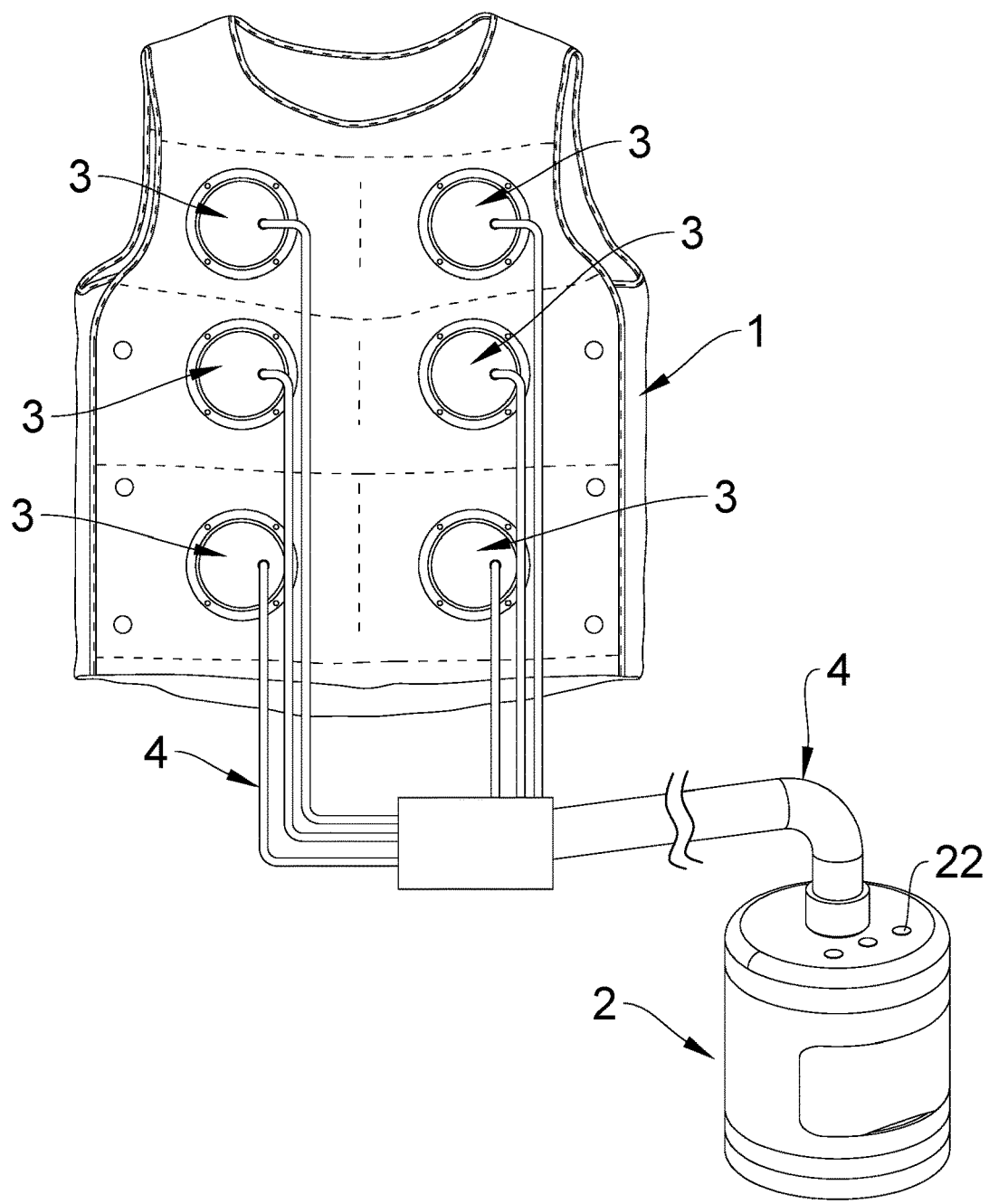
FIG. 1 is a schematic structural illustration of the present invention applied to a front side of a vest.
Figure 2:
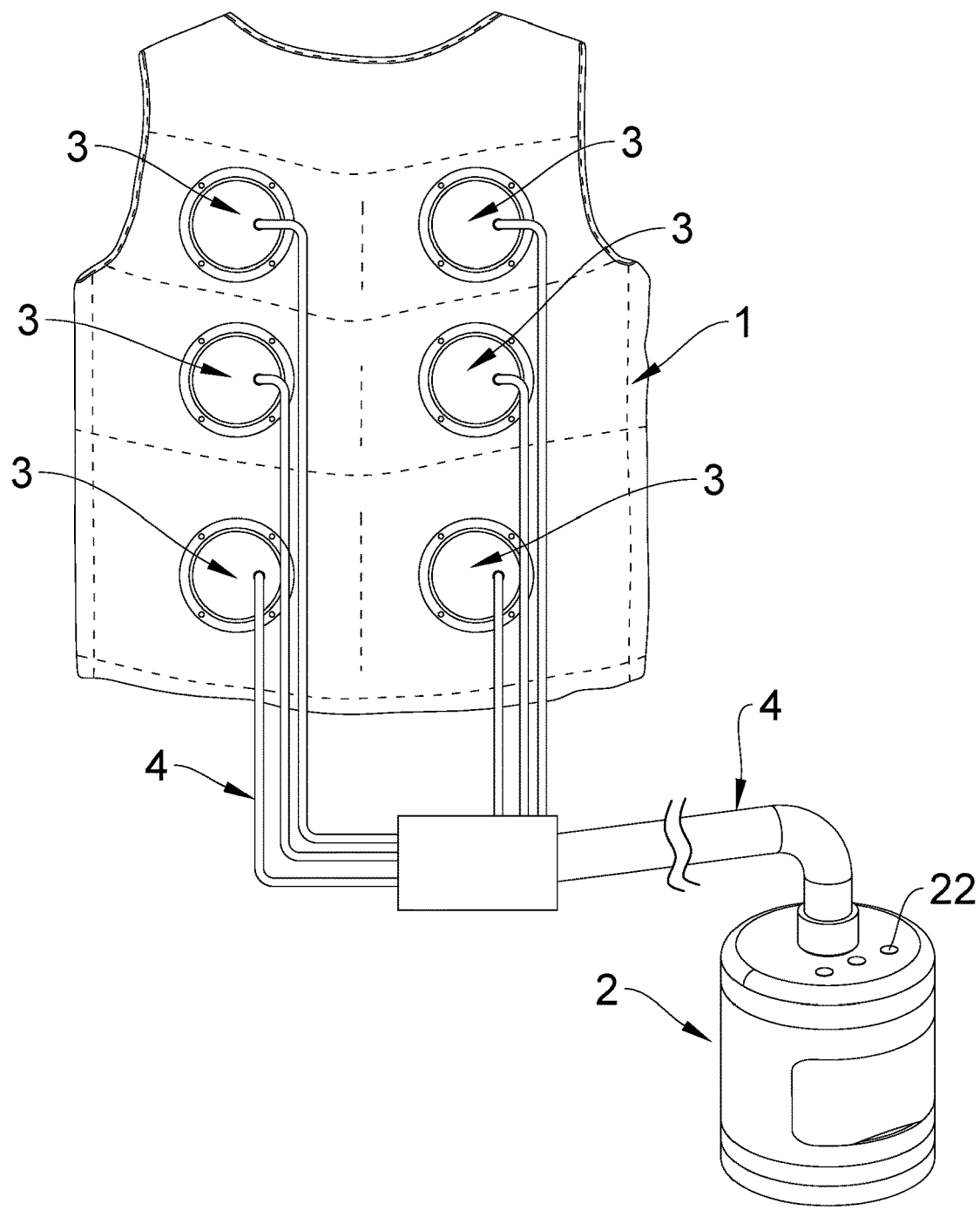
FIG. 2 is a schematic structural illustration of the present invention applied to a back side of a vest.

As shown in FIGS. 1-2, a medicine application device with ultrasonic massage enabling concentrated supply of medicine comprises several major components including a medicine concentrated supply device 2, at least one ultrasonic massage mechanism 3, a medicine supply pipe 42 and power cables 43 etc.

Figure 3:
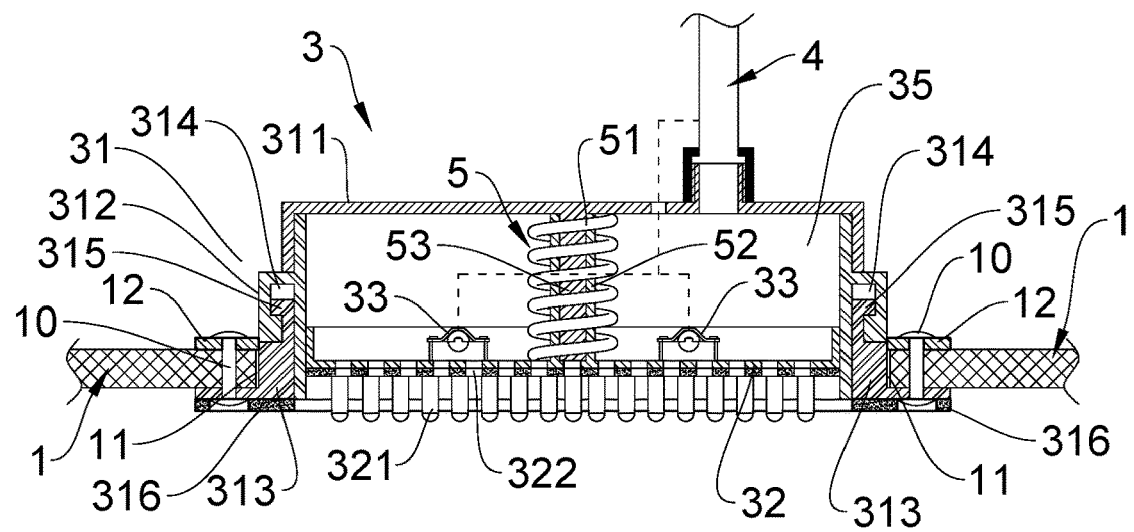
FIG. 3 is a sectional structural view of the ultrasonic massage mechanism of the present invention.
Figure 4:
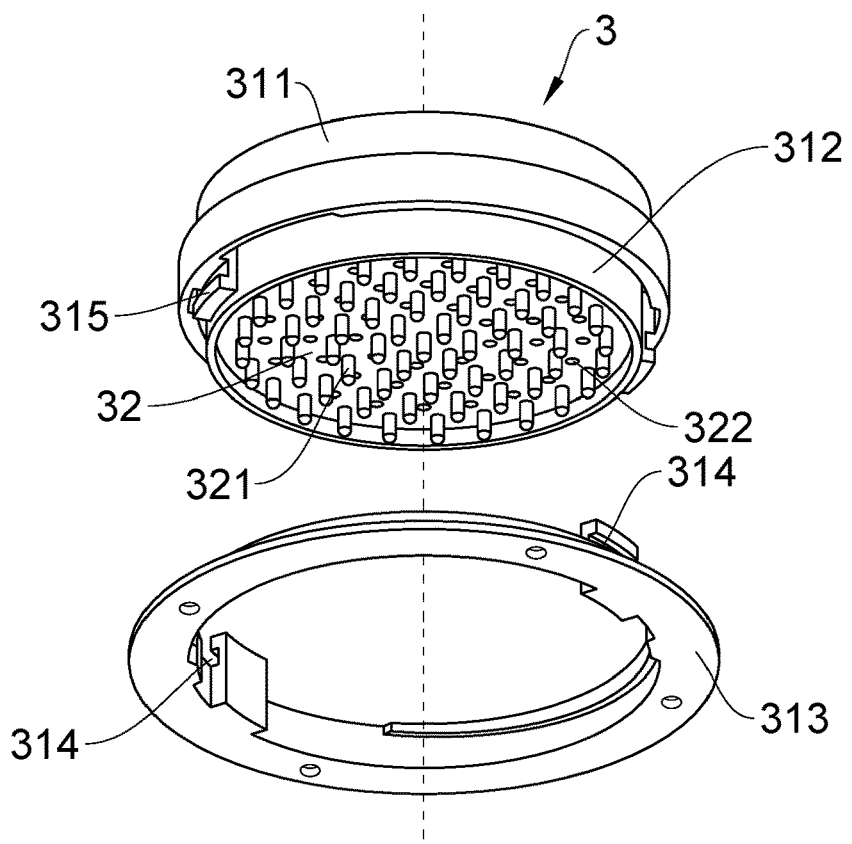
FIG. 4 is an exploded structural view of the ultrasonic massage mechanism.
Figure 14:
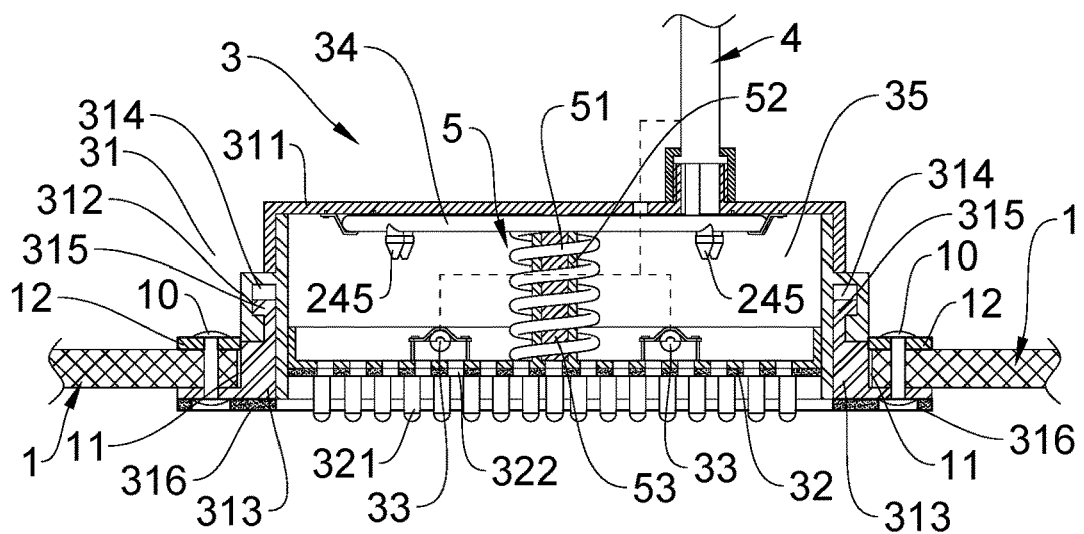
FIG. 14 is a sectional structural view of the ultrasonic massage mechanism according to an alternative embodiment.

As shown in FIGS. 3-4 or in FIG. 14, the ultrasonic massage mechanism 3 comprises a shell 31, a base panel 32 having massage projections 321, and an electrical ultrasonic vibration element 33; the base panel 32 is mounted at a bottom part of the shell 31; the electrical ultrasonic vibration element 33 is mounted on the base panel 32; the massage projections 321 make high frequency ultrasonic vibration to perform massage when driven by the electrical ultrasonic vibration element 33; the electrical ultrasonic vibration element 33 is a high frequency vibrating motor or an ultrasonic transducer.

When the high frequency vibrating motor is used, the motor has a rotating speed of 10,000 rpm, so that the massage projections 321 can make high frequency ultrasonic vibration. When the ultrasonic transducer is used, the vibration frequency is above 1 MHz. Quantity of the high frequency vibrating motor or the ultrasonic transducer provided will increase or decrease depending on the size and specification of the medicine application device of the present invention, on condition that the vibration frequency of the massage projections 321 is always above 1 Mhz. The vibration frequency of the massage projections 321 can be measured by a vibration measuring instrument.

Further, when the ultrasonic transducer is used, an ultrasonic generator or an ultrasonic generator circuit is provided on a circuit board 23. The ultrasonic transducer is driven to operate by the ultrasonic generator or the ultrasonic generator circuit.

As shown in FIGS. 3-4, to optimize the assembling structure of the ultrasonic massage mechanism 3 so that it can be more conveniently manufactured and processed, the shell 31 comprises an upper shell 311, a middle shell 312 and a lower shell 313; the base panel 32 is mounted inside a cavity enclosed by the middle shell 312; the upper shell 311 is mounted above the middle shell 312; an internal cavity 35 that allows temporary storage of the medicine and forms a passage way which the medicine can pass through is formed by a space enclosed by the upper shell 311, the middle shell 312 and the base panel 32. Due to provision of the internal cavity 35, when the medicine concentrated supply device 2 supplies medicine to the ultrasonic massage mechanism 3, atomized medicine will first reach the internal cavity 35, through which the atomized medicine is further released to the patient's skin via medicine release holes 322 provided on the base panel 32.

When the present invention is implemented in combination with a wearable item 1 and sold in the market as a complete and embodied technical solution, the lower shell 313 is also the component that enables connection between the ultrasonic massage mechanism 3 and the wearable item 1. As shown in FIG. 3 or FIG. 14, the lower shell 313 is fixedly mounted into a mounting hole 11 provided on the wearable item 1; the massage projections 321 are configured inside the wearable item 1 when the lower shell is fixedly mounted into the mounting hole, so that the massage projections 321 can come into contact with the patient's skin. As shown in FIG. 3 or FIG. 14, in order to further ensure that the shell 31 is firmly mounted to the wearable item 1, a fixing ring 12 may be provided on the wearable item above the lower shell 313 next to an opening of the mounting hole 11 from which the lower shell is inserted, and a screw 10 is used to lock the lower shell 313 and the fixing ring 12.

In actual implementation, to fulfil the need of therapy at different body parts, on the basis of the structures described above, the present invention can be implemented in combination with different wearable items to obtain an ultrasonic massage therapeutic device that is suitable for use in different body parts. The wearable item 1 can be a vest jacket, a piece of clothes, underwear, bra, underpants, socks, trousers, pants, joint protection sleeve, headwear, neck cover, glove, face mask, waist support, belt, halter top blouse, vest, or eye shield etc. To meet the user's requirements for use, the present invention can also be implemented in combination with various kinds of robots to obtain a robotic ultrasonic massage device for medicinal therapy that automatically or semi-automatically performs medicinal therapy and general health improving massage on patient's body.

Further, as shown in FIGS. 3 and 4, in order that the ultrasonic massage device mechanism 3 can be dismounted from the wearable item 1 for cleaning in its daily application, such that it can be conveniently mounted and dismounted, an outer side of the middle shell 312 is provided with at least one female buckling groove 314; the lower shell 313 is correspondingly provided with at least one male buckling piece 315. The male buckling piece 315 buckles to the female buckling groove 314 of the middle shell 312 to assemble the middle shell 312 and the lower shell 313.

Figure 15:
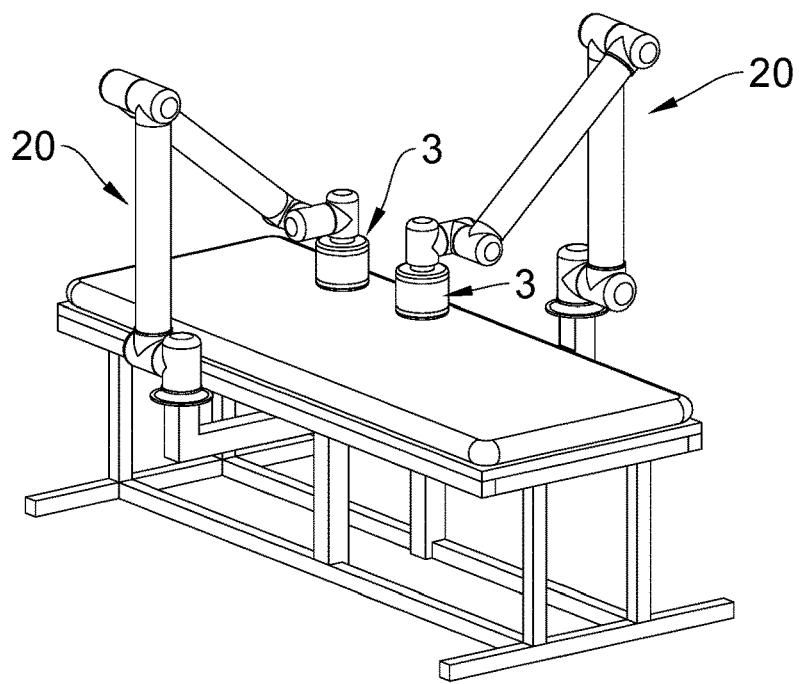
FIG. 15 is a schematic structural view of the present invention applied to a robot.
Figure 16:
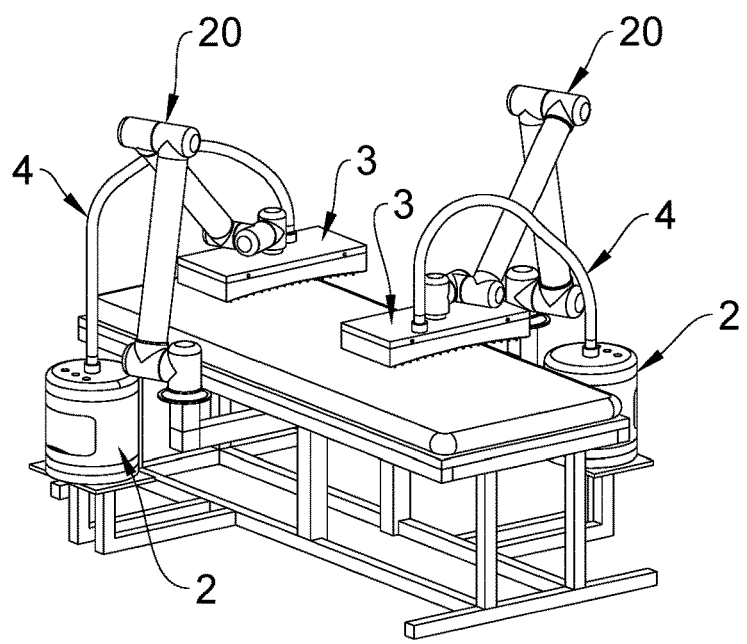
FIG. 16 is another schematic structural view of the present invention applied to a robot.

As shown in FIG. 15 or 16, apart from being used in combination with the wearable item 1, the present invention can also be used in combination with various kinds of robots to obtain a robotic ultrasonic massage device for medicinal therapy that automatically or semi-automatically performs medicinal therapy and general health improving massage on patient's body, so as to fulfil the user's requirements for use. Also, each of two sides of the ultrasonic massage mechanism 3 can be provided with an ear, and each ear has an opening for a string to pass through. As such, each ear can be tied with a string, and the ultrasonic massage mechanism 3 can be tied to a targeted body part via the string to perform ultrasonic massage and medicinal therapy.

As shown in FIG. 3 or FIG. 14, a flexible resilience mechanism 5 comprising a spring 51, a sleeve 52 and a core rod 53 is provided inside the ultrasonic massage mechanism corresponding to the upper shell 311 and the middle shell 312, wherein a top end of the core rod 53 is connected to the upper shell 311; a bottom end of the sleeve 52 is connected to the top surface of the base panel 32; a top end of the sleeve 52 receives insertion of the core rod 53 from a bottom end thereof; the spring 51 winds around the sleeve 52 that sleeves the core rod 53. Due to this flexible resilience mechanism 5, the base panel 32 and the massage projections 321 thereon can always be in sufficiently close contact with the patient's skin to provide vibration and massage, while not pressing too tightly against the patient's skin. Therefore, vibration and massage are more comfortable, and thereby promoting blood circulation in the body. Besides, a soft rubber gasket ring 316 is provided at a bottom surface of the lower shell 313 to come into contact and support against the patient's skin so as to further increase the comfort of using the present invention and also preventing or at least delaying leakage of medicine molecules to the outer environment.

Further, it should be noted that, the size and outer appearance of the ultrasonic massage mechanism 3 can be determined and manufactured in accordance with specific needs during actual use. In the embodiments shown in FIG. 15 or 16, there is no specific limitation with respect to the size and outer appearance of the ultrasonic massage mechanism. There is also no specific limitation with respect to the quantity of the ultrasonic massage mechanism 3 being used. As shown in FIGS. 1 and 2, several ultrasonic massage mechanisms 3 can be used in combination with one medicine concentrated supply device 2. Alternatively, as shown in FIG. 15 or 16, only one ultrasonic massage mechanism 3 can be used in combination with one medicine concentrated supply device 2.

As shown in FIG. 5, FIG. 9, FIG. 10 or FIG. 13, the medicine concentrated supply device 2 comprises a housing 21, a control panel 22, a circuit board 23, and a medicine supply device 24; wherein the control panel 22 is provided on a surface of the housing 21; the circuit board 23 is mounted inside the housing 21; the control panel 21 and the circuit board 23 are electrically connected. The medicine supply device 24 is mounted in the housing 21 and is electrically connected with the circuit board 23; the medicine supply device 24 is connected with the ultrasonic massage mechanism 3 via the medicine supply pipe 42 to supply medicine to the ultrasonic massage mechanism 3; a plurality of medicine release holes 322 are provided on the base panel 32 to release medicine to the patient's skin; the electrical ultrasonic vibration element 33 is electrically connected with the circuit board 23.

Also, an intelligent IC chip, a Bluetooth communication module, and a WIFI module etc can be put into the circuit board 23 during actual implementation of the present invention. Corresponding control applications can be developed to achieve control by smart phones and tablet computers.

Figure 6:
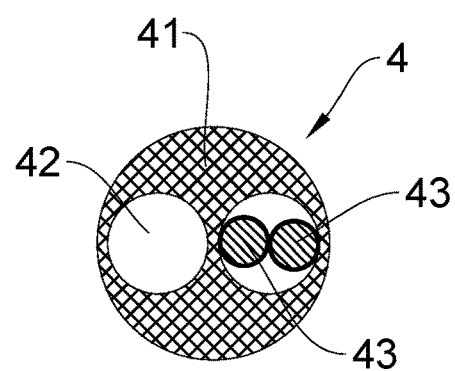
FIG. 6 is a sectional structural view of a compound piping of the present invention.

As shown in FIG. 6, in order that the medicine supply pipe 42 and the power cables 43 are arranged neatly and can be conveniently used, the present invention also comprises a compound piping 4, comprising a pipe jacket 41, and the medicine supply pipe 42 and the power cables 43 disposed inside the pipe jacket 41. The medicine supply pipe 42 supplies medicine from the medicine concentrated supply device 2 to the ultrasonic massage mechanism 3. The power cables 43 connect the ultrasonic massage mechanism 3 and the medicine concentrated supply device 2 electrically.

In order to fulfil the therapeutic requirements in the use of different types of medicine, the medicine concentrated supply device 24 provided by the present invention has several embodiments which will be described in detail below.

Figure 5:
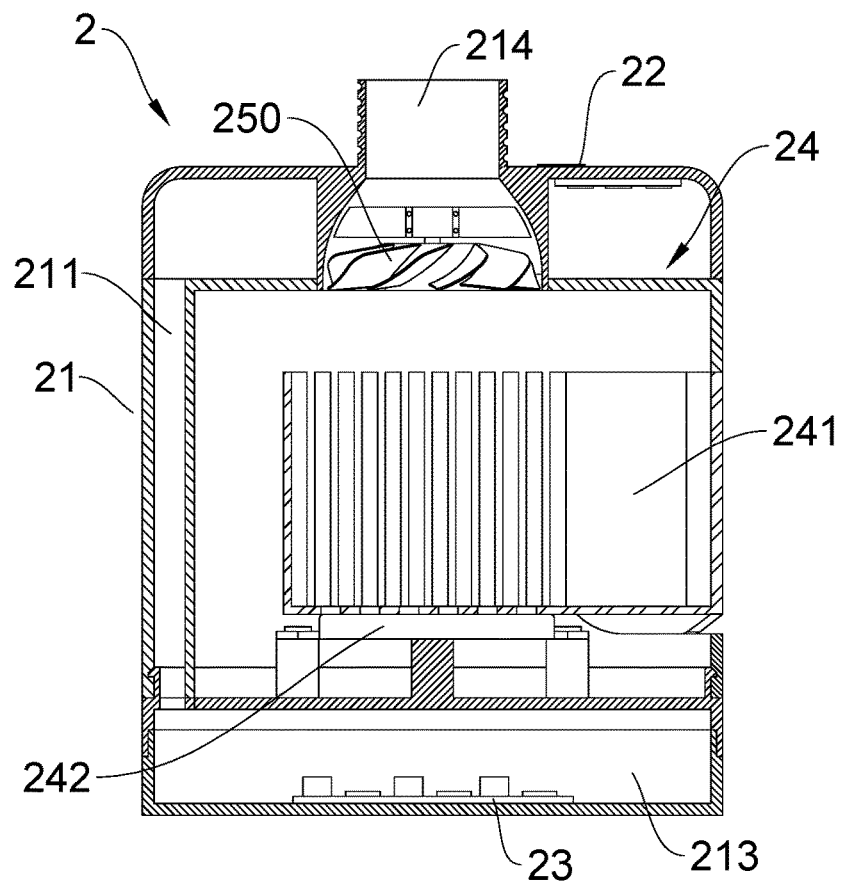
FIG. 5 is a sectional structural view of a medicine concentrated supply device according to embodiment 1 of the present invention.
Figure 7:
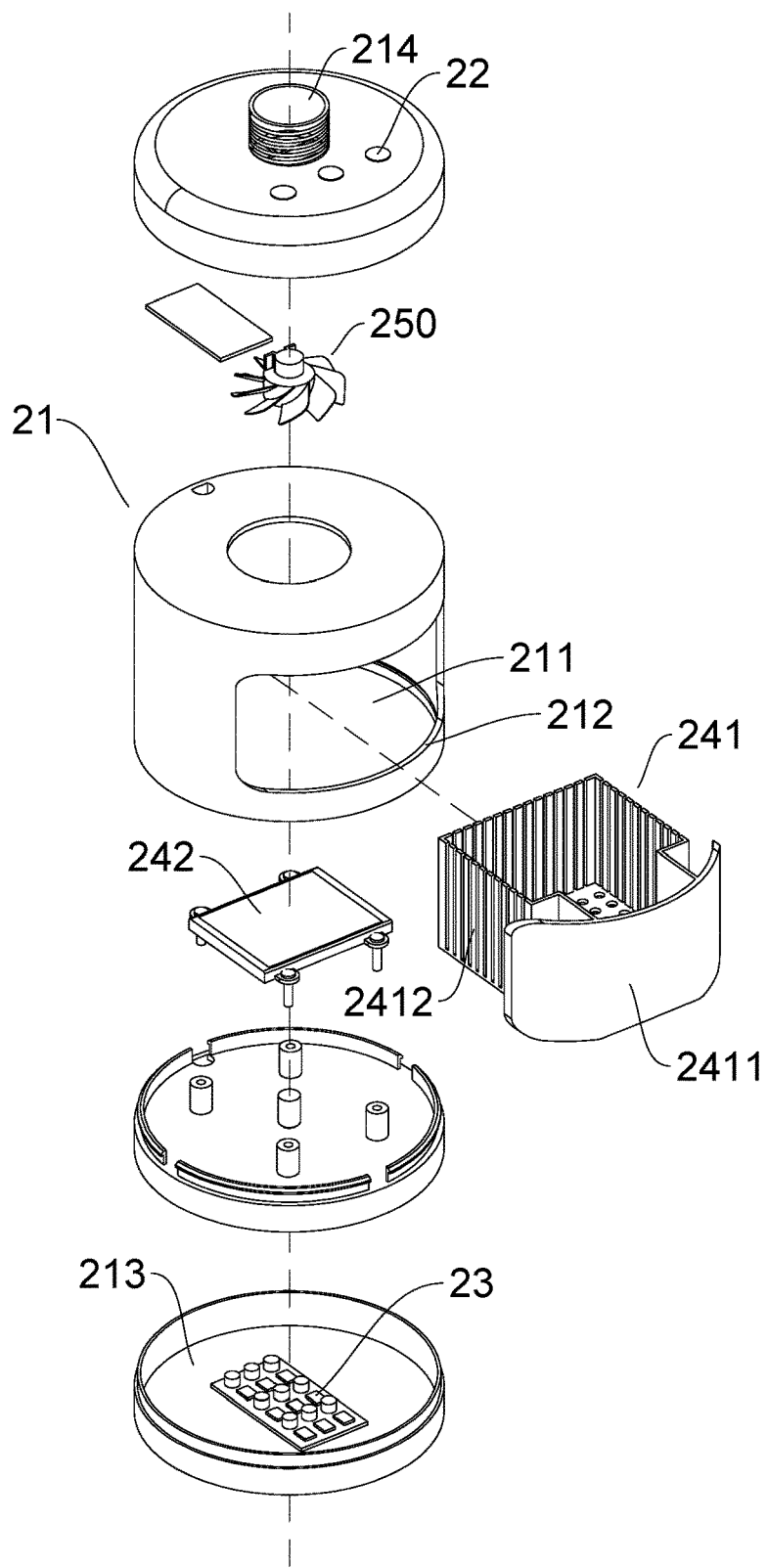
FIG. 7 is an exploded structural view of the medicine concentrated supply device according to embodiment 1 of the present invention.

As shown in FIG. 5 and FIG. 7, the medicine concentrated supply device 24 is implemented as an electrically heating and volatilizing device for solid form medicine, comprising a medicine chamber 241, an electrical heating plate 242, and a booster fan 250; so that medicine molecules are volatilized from the solid form medicine by using the electrical heating plate 242 and supplied to the ultrasonic massage mechanism 3. The medicine molecules are being increased in pressure by using the booster fan 250 so that the medicine molecules move in the air flow created by the booster fan and are quickly supplied to the ultrasonic massage mechanism 3.

According to a specific and preferred embodiment of the medicine concentrated supply device implemented as the electrically heating and volatilizing device for solid form medicine, the medicine chamber 241 is configured as a drawer that stores medicine. The housing is provided with a groove 211 to accommodate the medicine chamber 241 and an access opening 212; the medicine chamber 241 is inserted into the groove 211 of the housing 21 through the access opening 212. The medicine chamber 241 is formed by a front panel 2411 and a medicine storage trough 2412. To use the medicine chamber, pull open the medicine chamber 241, place medicine into the medicine storage trough 2412, and then push back the medicine chamber 241. As shown in FIG. 5, a bottom portion of the housing 21 is also provided with a circuit chamber 213; the circuit board 23 is mounted inside the circuit chamber 213; the electrical heating plate 242 is disposed inside the housing 21 between the circuit chamber 213 and the groove 211; the electrical heating plate 242 is electrically connected with the circuit board 23. By configuring the circuit chamber 213 at a bottom portion of the housing 21, better heat dissipation of the circuit board 23 can be achieved, thereby lengthening the service life of the circuit board 23; better heat dissipation is achieved because hot air will rise according to known physical principle, therefore, heat produced by the electrical heating plate 242 will rise instead of sink, thereby protecting the circuit board. 23. As shown in FIG. 5, a booster fan 250 is mounted inside the housing 21 at a position above the groove 211; a piping port 214 is provided at a top surface of the housing 21; the piping port 214 is connected with the ultrasonic massage mechanism 3 via the medicine supply pipe 42. Therefore, by using the booster fan 250, medicine molecules released by heating up the medicine can be quickly blown towards the ultrasonic massage mechanism 3 along with a hot stream of air, and during massage of a targeted body part by the ultrasonic massage mechanism 3, the medicine molecules pass through the medicine release holes 322 on the ultrasonic massage mechanism 3 to warm the targeted body part, so as to increase the efficiency and results of medicinal therapy.

Figure 8:
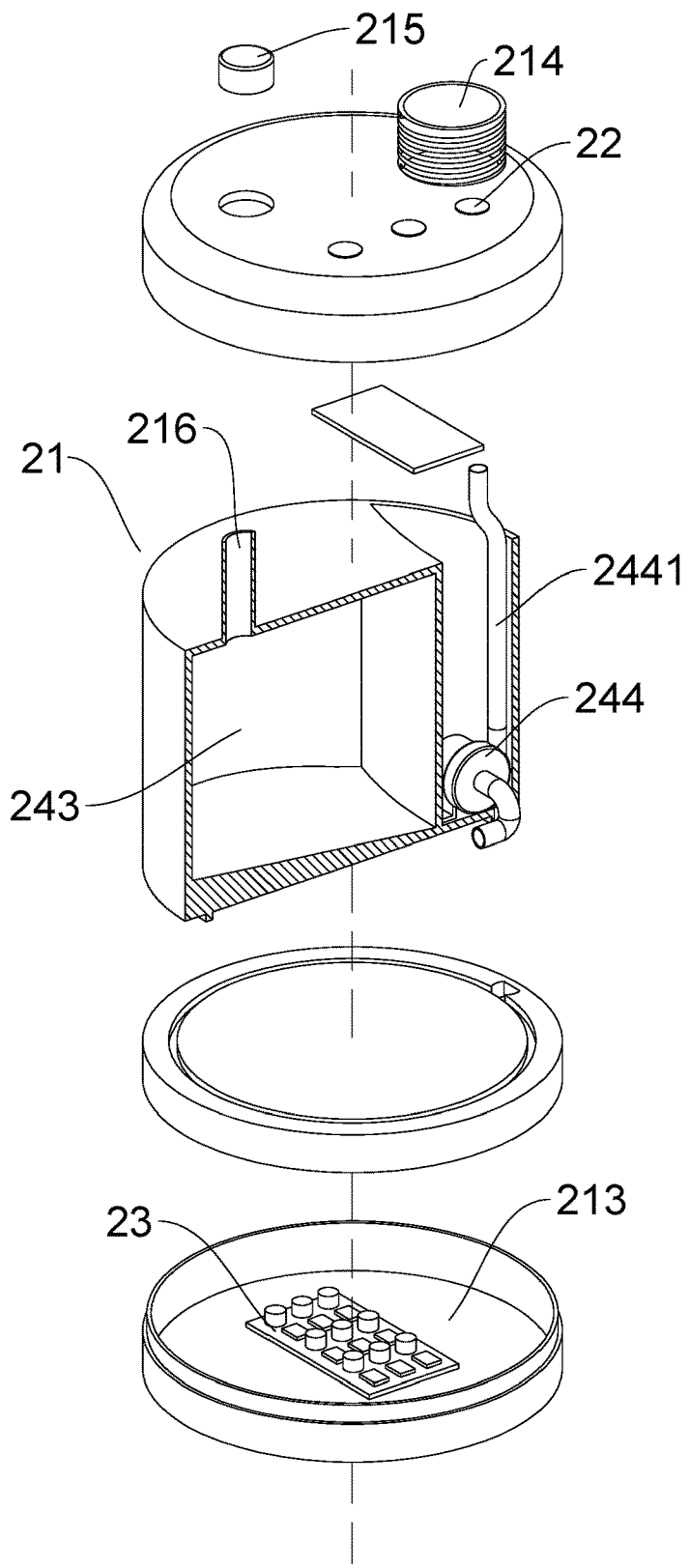
FIG. 8 is an exploded structural view of the medicine concentrated supply device according to embodiment 2 of the present invention.
Figure 9:
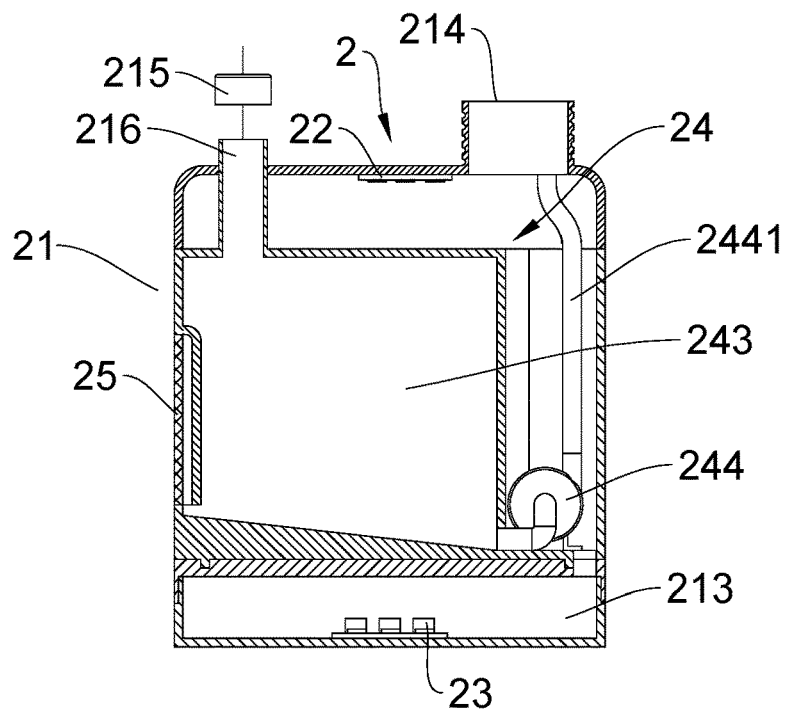
FIG. 9 is a sectional structural view of the medicine concentrated supply device according to embodiment 2 of the present invention.

As shown in FIGS. 8-9, the medicine supply device 24 can be implemented as a liquid form medicine spraying device, comprising a liquid storage box 243, a liquid suction pump 244 and a plurality of mist spray nozzles 245. The mist spray nozzles 245 are mounted at the ultrasonic massage mechanism 3 (FIG. 14). By means of the liquid suction pump 244 and the mist spray nozzles 245, the liquid form medicine is increased in pressure and ejected as mist so as to supply medicine to the ultrasonic massage mechanism 3. The liquid form medicine spraying device has the following difference compared with the electrically heating and volatilizing device for solid form medicine: The liquid form medicine spraying device makes use of the liquid suction pump 244 to pump and increase the pressure of the liquid medicine, which is then sprayed to a targeted body part through the mist spray nozzles 245, and by using the ultrasonic massage mechanism 3 to perform high frequency vibration and massage on the targeted body part, the liquid medicine can be quickly absorbed by human body, thereby achieving the effects of both massage and medicinal therapy.

A detailed preferred embodiment of this kind of liquid form medicine spraying device is as follows: the liquid storage box 243 is provided inside the housing 21; the housing 21 is provided with a liquid adding inlet 216 connected with the liquid storage box 243; the liquid adding inlet 216 is also provided with a cap 215. The liquid suction pump 244 is mounted inside the liquid storage box 243 or inside the housing 21; a liquid inlet end of the liquid suction pump 244 is connected with the liquid storage box 243; a liquid outlet end of the liquid suction pump 244 is connected with a liquid outlet tube 2441; the liquid outlet tube 2441 is configured to extend out of the housing 21 and is connected with the piping port 214 provided on the housing 21. As shown in FIGS. 8-9, a bottom portion of the housing 21 is likewise provided with a circuit chamber 213; the circuit board 23 is mounted inside the circuit chamber 213; the liquid suction pump 244 and the circuit board 23 are electrically connected. In order that the liquid medicine can be sprayed on the base panel 32 evenly and then released to the targeted body part through the medicine release holes 322, the ultrasonic massage mechanism 3 is also provided with a ring shaped tube 34 as shown in FIG. 14. The mist spray nozzles 245 are provided on the ring shaped tube 34 spraying the liquid form medicine towards the medicine release holes 322 on the base panel 32. The ring shaped tube 34 is in communication with the piping port 214 through the medicine supply pipe 42.

Figure 10:
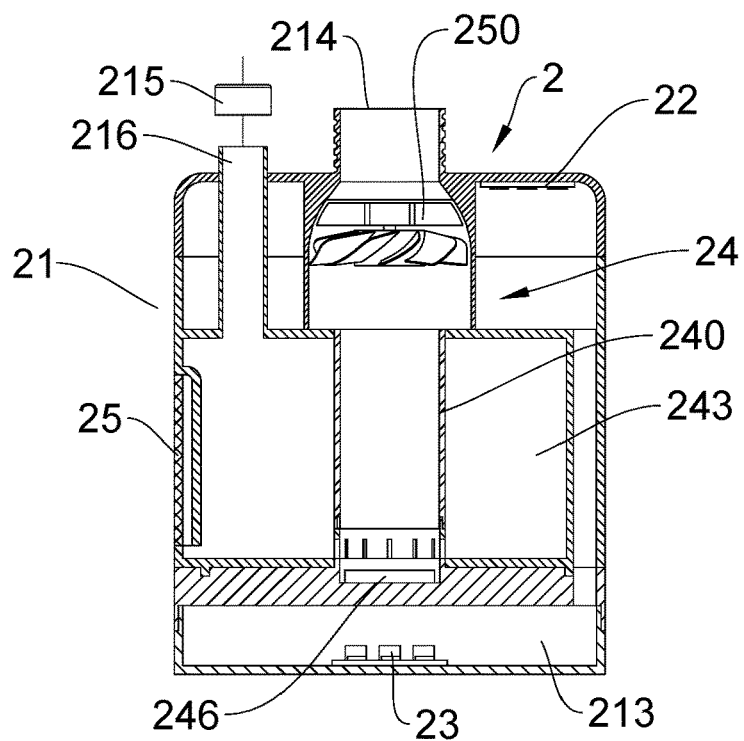
FIG. 10 is a sectional structural view of the medicine concentrated supply device according to embodiment 3 of the present invention.
Figure 11:
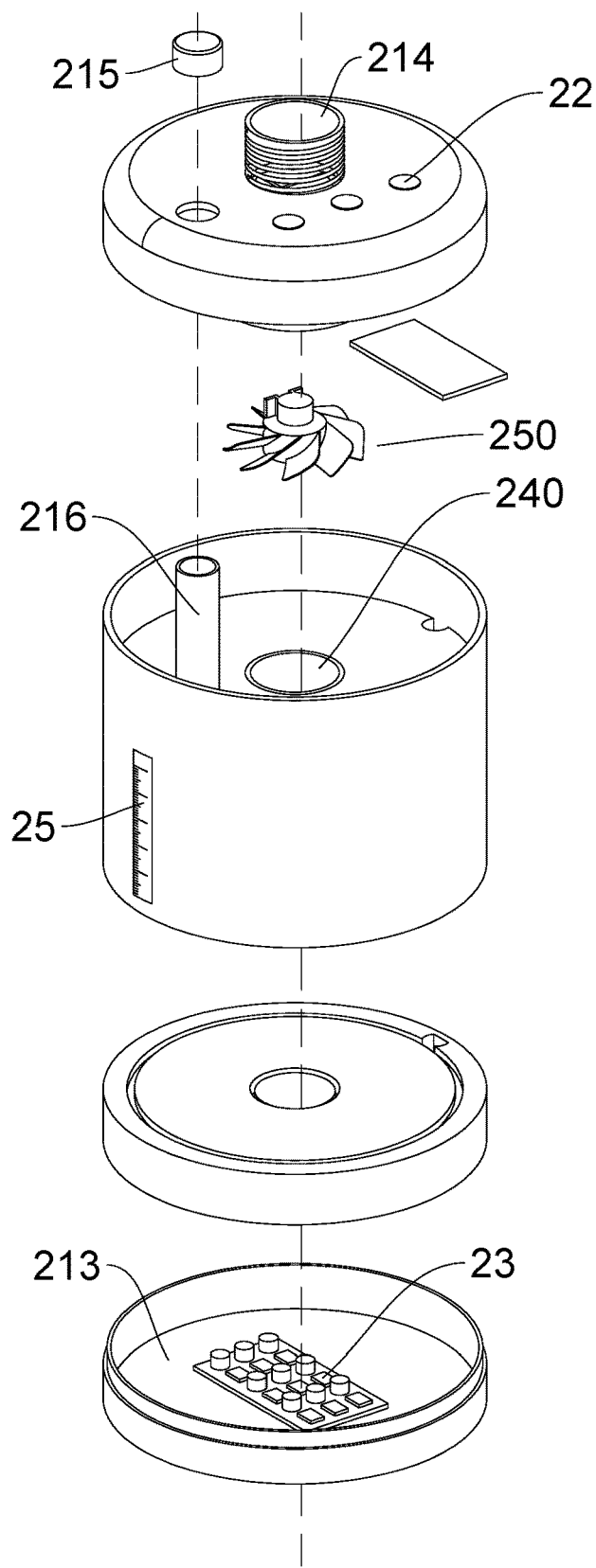
FIG. 11 is an exploded structural view of the medicine concentrated supply device according to embodiment 3 of the present invention.

As shown in FIGS. 10-11, the medicine supply device 24 can be implemented as an ultrasonically atomized liquid form medicine spraying device, comprising a liquid storage box 243, an ultrasonic atomizing module 246, and a booster fan 250, so that the ultrasonic atomizing module 246 will atomize the liquid form medicine ultrasonically, and the atomized liquid form medicine will be sprayed to the ultrasonic massage mechanism 3. The ultrasonically atomized liquid form medicine spraying device has the following difference from the liquid form medicine spraying device described above: the described liquid form medicine spraying device pressurizes the liquid medicine which is then sprayed directly through the mist spray nozzles 245. However, the ultrasonically atomized liquid form medicine spraying device as currently described atomizes liquid medicine by the ultrasonic atomizing module 246, and then the atomized liquid medicine is sprayed to the ultrasonic massage mechanism 3 for further utilization.

A detailed embodiment of the ultrasonically atomized liquid form medicine spraying device is as follows: As shown in FIGS. 10-11, the liquid storage box 243 of the ultrasonically atomized liquid form medicine spraying device is disposed inside the housing 21. A liquid adding inlet 216 connected with the liquid storage box 243 is provided on the housing 21; the liquid adding inlet 216 is provided with a cap 215. The ultrasonic atomizing module 246 is provided inside the housing 21 and is in communication with the inside of the liquid storage box 243; a mist guiding tube 240 is also provided in the liquid storage box 243; the mist guiding tube 240 is connected with a piping port 214 provided on the housing 21; the booster fan 250 is disposed at a position between the mist guiding tube 240 and the piping port 214. The ultrasonic atomizing module 246 is the same as a known ultrasonic atomizing module in a humidifier, and therefore will not be described in detail here. As described above, a bottom portion of the housing 21 is also provided with a circuit chamber 213; the circuit board 23 is mounted inside the circuit chamber 213. The ultrasonic atomizing module 246, the booster fan 250 and the circuit board 23 are electrically connected. The structure and operating principle of the ultrasonic atomizing module 246 are the same as the one used in a prior art ultrasonic humidifier.

Figure 12:
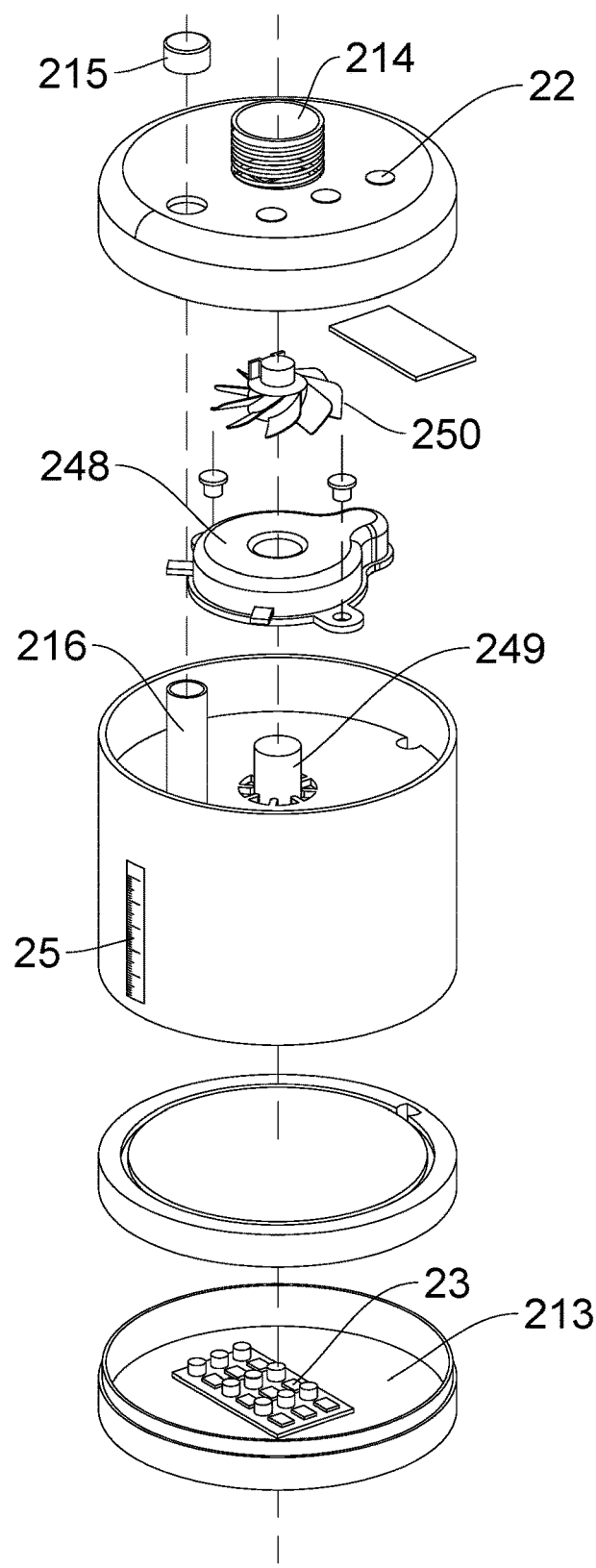
FIG. 12 is an exploded structural view of the medicine concentrated supply device according to embodiment 4 of the present invention.
Figure 13:
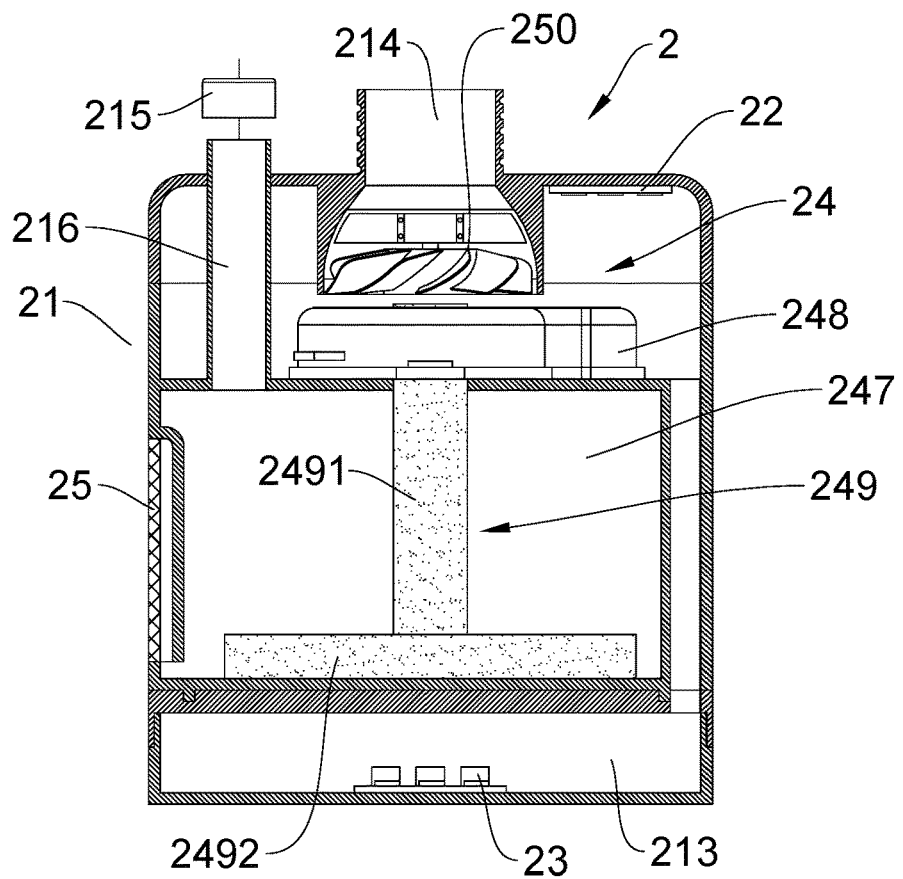
FIG. 13 is a sectional structural view of the medicine concentrated supply device according to embodiment 4 of the present invention.

As shown in FIGS. 12-13, the medicine supply device 24 can be implemented as an electrical heating and volatilizing device for liquid form medicine, comprising a liquid storage container 247, an electrical heating ring 248, a liquid suction body 249, and a booster fan 250, wherein one end of the liquid suction body 249 is configured to be inserted into the liquid storage container 247, and another end of the liquid suction body 249 is configured to be sleeved within the electrical heating ring 248, so that the electrical heating ring 248 will volatilize the liquid medicine to give out medicine molecules and then supply the medicine molecules to the ultrasonic massage mechanism 3. The electrical heating and volatilizing device for liquid form medicine has the following difference compared with the electrically heating and volatilizing device for solid form medicine: The electrical heating and volatilizing device for liquid form medicine as currently described heats up the liquid medicine to volatilize the liquid medicine to give out medicine molecules, and then the medicine molecules are pressurized and transported by the booster fan 250 to the ultrasonic massage mechanism 3 for further utilization.

A detailed embodiment of the electrical heating and volatilizing device for liquid form medicine is as follows: As shown in FIGS. 12-13, the liquid storage container 247 is provided inside the housing 21; a liquid adding inlet 216 connected with the liquid storage container 247 is provided on the housing 21; the liquid adding inlet 216 is provided with a cap 215; the electrical heating ring 248 is provided in the housing 21 at a position above the liquid storage container 247; one end of the liquid suction body 249 is configured to be inserted into the liquid storage container 247, and another end of the liquid suction body 249 is configured to be sleeved within the electrical heating ring 248. A piping port 214 is correspondingly provided in the housing 21 at a position above the electrical heating ring 248. The booster fan 250 is provided inside the housing at a position between the electrical heating ring 248 and the piping port 214; the piping port 214 is connected with the ultrasonic massage mechanism 3 through the medicine supply pipe 42. A bottom portion of the housing 21 is also provided with a circuit chamber 213; the circuit board 23 is mounted inside the circuit chamber 213; the electrical heating ring 248, the booster fan 250 and the circuit board 23 are electrically connected. As shown in FIG. 13, in order that the liquid suction body 249 can suction all the liquid in the liquid storage container 247 no matter if the liquid storage container 247 is disposed vertically or horizontally, the liquid suction body 249 comprises a liquid suction rod 2491 and a liquid suction plate 2492; the liquid suction plate 2492 is disposed inside the liquid storage container 247; one end of the liquid suction rod 2491 is configured to be inserted into the liquid storage container 247 and is connected with the liquid suction plate 2492; another end of the liquid suction rod 2491 is configured to be sleeved within the electrical heating ring 248.

In order that users can observe the remaining amount of liquid medicine in the liquid storage box 243 or liquid storage container 247 any time during use, FIGS. 9, 10, 11, 12, 13 show a liquid level indicator 25 connected with the liquid storage box 243 or the liquid storage container 247, provided on a side surface of the housing 21.

Also, during implementation of the embodiments described above, particularly in the embodiment using electrical heating to volatilize the medicine, a temperature sensor should be provided to increase safety during use.

What is claimed is:

1. A medicine application device, comprising a medicine concentrated supply device (2), at least one ultrasonic massage mechanism (3), a medicine supply pipe (42) and power cables (43); wherein,
the ultrasonic massage mechanism (3) comprises a shell (31), a base panel (32) having massage projections (321), and an electrical ultrasonic vibration element (33); the base panel (32) is mounted at a bottom part of the shell (31); the electrical ultrasonic vibration element (33) is mounted on the base panel (32);
the massage projections (321) make high frequency ultrasonic vibration to perform massage when driven by the electrical ultrasonic vibration element (33);
the electrical ultrasonic vibration element (33) is a high frequency vibrating motor or an ultrasonic transducer;
the medicine concentrated supply device (2) comprises a housing (21), a control panel (22), a circuit board (23), and a medicine supply device (24); wherein the control panel (22) is provided on a surface of the housing (21); the circuit board (23) is mounted inside the housing (21); the control panel (21) and the circuit board (23) are electrically connected; the medicine supply device (24) is mounted in the housing (21) and is electrically connected with the circuit board (23); the medicine supply device (24) is connected with the ultrasonic massage mechanism (3) via the medicine supply pipe (42) to supply medicine to the ultrasonic massage mechanism (3); a plurality of medicine release holes (322) are provided between the massage projections (321) on the base panel (32) to release medicine; the electrical ultrasonic vibration element (33) is electrically connected with the circuit board (23) via the power cables (43);
wherein the medicine supply device (24) is implemented as an electrical heating and volatilizing device for liquid form medicine, comprising a liquid storage container (247), an electrical heating ring (248), a liquid suction body (249), and a booster fan (250), wherein one end of the liquid suction body (249) is configured to be inserted into the liquid storage container (247), and another end of the liquid suction body (249) is configured to be sleeved within the electrical heating ring (248), so that the electrical heating ring (248) volatilizes the liquid form medicine to give out medicine molecules and then supplies the medicine molecules to the ultrasonic massage mechanism (3);
the shell (31) comprises an upper shell (311), a middle shell (312) and a lower shell (313); the base panel (32) is mounted inside a cavity enclosed by the middle shell (312): the upper shell (311) is mounted above the middle shell (312);
an internal cavity (35) that allows temporary storage of the medicine and forms a passage way which the medicine is configured to pass through is formed by a space enclosed by the upper shell (311), the middle shell (312) and the base panel (32); an outer side of the middle shell (312) is provided with at least one female buckling groove (314); the lower shell (313) is correspondingly provided with at least one male buckling piece (315): and the male buckling piece (315) buckles to the female buckling groove (314) of the middle shell (312) to assemble the middle shell (312) and the lower shell (313).

2. The medicine application device of claim 1, further comprises a flexible resilience mechanism (5) inside the ultrasonic massage mechanism corresponding to the upper shell (311) and the middle shell (312), the flexible resilience mechanism (5) comprises a spring (51), a sleeve (52) and a core rod (53); wherein a top end of the core rod (53) is connected to the upper shell (311); a bottom end of the sleeve (52) is connected to the top surface of the base panel (32); a top end of the sleeve (52) receives insertion of the core rod (53) from a bottom end thereof; the spring (51)

winds around the sleeve (52) that sleeves the core rod (53); and a rubber gasket ring (316) is provided at a bottom surface of the lower shell (313).

3. The medicine application device of claim 1, wherein when the medicine supply device is implemented as the electrical heating and volatilizing device for liquid form medicine, the liquid storage container (247) is provided inside the housing (21); a liquid adding inlet (216) connected with the liquid storage container (247) is provided on the housing (21); the liquid adding inlet (216) is provided with a cap (215);

the electrical heating ring (248) is provided in the housing (21) at a position above the liquid storage container (247); a piping port (214) is correspondingly provided in the housing (21) at a position above the electrical heating ring (248);

the booster fan (250) is provided inside the housing (21) at a position between the electrical heating ring (248) and the piping port (214); the piping port (214) is connected with the ultrasonic massage mechanism (3) through the medicine supply pipe (42);

a bottom portion of the housing (21) is also provided with a circuit chamber (213);

the circuit board (23) is mounted inside the circuit chamber (213); the electrical heating ring (248), the booster fan (250) and the circuit board (23) are electrically connected.

4. The medicine application device of claim 3, wherein the liquid suction body (249) comprises a liquid suction rod (2491) and a liquid suction plate (2492); the liquid suction plate (2492) is disposed inside the liquid storage container (247); one end of the liquid suction rod (2491) is configured to be inserted into the liquid storage container (247) and is connected with the liquid suction plate (2492); and another end of the liquid suction rod (2491) is configured to be sleeved within the electrical heating ring (248).

5. The medicine application device of claim 1, further comprising a compound piping (4); the compound piping (4) comprises a pipe jacket (41), and the medicine supply pipe (42) and the power cables (43) are disposed inside the pipe jacket (41).

* * * * *